United States Patent [19]

Burghoffer et al.

[11] Patent Number: 4,640,140
[45] Date of Patent: Feb. 3, 1987

[54] AEROSOL SAMPLER WITH CASCADE IMPACTION AND UNIFORM DEPOSITION

[75] Inventors: Patrick Burghoffer, Lognes; Michel Pourprix, Montlhery; Patrick Poussier, Vincennes, all of France

[73] Assignee: Commissariat a l'Energie Atomique, Paris, France

[21] Appl. No.: 684,864

[22] Filed: Dec. 21, 1984

[30] Foreign Application Priority Data

Dec. 23, 1983 [FR] France ................ 83 20697

[51] Int. Cl.⁴ .............................. G01N 1/24
[52] U.S. Cl. ................................. 73/863.22
[58] Field of Search ..................... 73/863.22

[56] References Cited

U.S. PATENT DOCUMENTS

| 2,682,771 | 7/1954 | Parker | 73/863.22 X |
| 2,894,877 | 7/1959 | Sinden | |
| 3,518,815 | 7/1970 | McFarland et al. | 73/863.22 |
| 3,693,457 | 9/1972 | Pilat | 73/432 PS |
| 4,321,822 | 3/1982 | Marple et al. | 73/863.22 X |

FOREIGN PATENT DOCUMENTS

| 2853615 | 6/1980 | Fed. Rep. of Germany | 73/863.22 |
| 781664 | 11/1980 | U.S.S.R. | 73/863.22 |

OTHER PUBLICATIONS

"A New Personal Dust Sampler, the CIP"; *Atmospheric Pollution* 1978; Proceedings of the 13th International Colloquium; Paris, France; *Studies in Environmental Science;* vol. I; pp. 83–86; Apr.-1978; P. Courbon.

"A Collection Device for Capturing a Spray Sample"; *J. Phys. E: Sci. Instrum.;* vol 11, No. 6, pp. 525–528; Jun.-1978; William S. Janna et al.

*Primary Examiner*—Stewart J. Levy
*Assistant Examiner*—Tom Noland
*Attorney, Agent, or Firm*—Michael N. Meller

[57] ABSTRACT

An apparatus of the aerosol sampler type with cascade impaction and uniform deposition comprising a conical air inlet fixed to a tight, hollow, cylindrical chamber of revolution constituted by the superimposing of several stages in the form of hollow cylinders of revolution traversed by the air flow from the conical inlet and each having a circular plate perforated with holes located on concentric circles coaxial to the plate and having an identical diameter progressively decreasing in each stage, as well as a collection disk located downstream of the perforated plate and whose diameter is smaller than the internal diameter of the impacter chamber, incorporating a pump for ensuring the vertical downward circulation of the air and driving gears for the relative rotation of each perforated plate with respect to the corresponding collection disk, wherein in each stage the axis of rotation of the disk passes through the disk and is offset relative to the axis of the circular perforated plate.

9 Claims, 5 Drawing Figures

AEROSOL SAMPLER WITH CASCADE IMPACTION AND UNIFORM DEPOSITION

BACKGROUND OF THE INVENTION

The present invention relates to an apparatus for the granulometric analysis of aerosols by cascade impaction and uniform deposition having a conical air inlet fixed to a tight, hollow cylindrical chamber of revolution constituted by superimposing several stages in the form of hollow cylinders. Each stage is traversed by the air flow from the conical inlet and each stage has a circular plate perforated by holes located on concentric circles coaxial to said plate, the holes in each stage having identical diameters while the hole diameter progressively decreases in successive stages, as well as a collection disk positioned downstream of the perforated plate whose diameter is less than the internal diameter of the stage, incorporates means for ensuring the downwardly vertical circulation of air and means for relatively rotating each perforated plate with respect to the corresponding collection disk.

The operating mode of this known apparatus is based on the granulometric separation of aerosols, as a function of their kinetic energy, i.e. their inertia.

According to the prior art, the function of such an apparatus is the recovery of an adequate quantity of aerosols in order to have the necessary sensitivity for the exploitation of the results of the weighing operations, chemical analysis, counting the radioactivity or the X-fluorescene, etc. One known apparatus of this type is called the Andersen sampler, which comprises a stack of cylindrical hollow stages in which the aerosol circulates, each stack has a fixed plate perforated with calibrated holes and a collection disk, positioned downstream of the perforated plate, on which the particles are deposited by inertia.

Initially, an apparatus of the aforementioned type was used, whose collection disk was fixed. The deposit which collected on the collection disk was then localized on a very small surface area substantially corresponding to the projected surface of the holes formed in the perforated plate. This apparatus suffered from three main disadvantages which limited the quantity of aerosols collected, namely (a) the modification of the impaction characteristics of a given stage when the thickness of the deposit increased, (b) the reentrainment of aerosols from one stage towards the lower stages in the case of an excessive increase in the thickness of the deposit and (c) the auto-absorption caused by superimposing particles in the case of counting α-radioactivity or the deterioration of the emission spectrum of the radiation.

In order to obviate the aforementioned disadvantages, a collection method consisting of displacing the collection plates has already been envisaged, the collection disk rotating about its axis, which axis coincides with the axis of revolution symmetry of the cylindrical impacter. In this case, on the collection disks there are circular deposits of particles whose width is substantially equal to the projected surface of the holes formed in the perforated plate. Such a deposit reduces the disadvantages referred to hereinbefore, but fails to eliminate them.

SUMMARY OF THE INVENTION

The present invention relates to an aerosol sampler with cascade impaction and uniform deposition which, by using simple means, makes it possible to overcome the prior art difficulties referred to hereinbefore.

This apparatus, in per se known manner, comprises a conical air inlet fixed to a tight, hollow cylindrical chamber of revolution, constituted by the superimposing of several stages in the form of hollow cylinders of revolution traversed by an air flow from the conical inlet. Each stage has a circular plate perforated by holes located along several concentric circles coaxial to said plate and having identical diameters. The hole diameter decreases progressively in successive stages. A collection disk is positioned downstream of the perforated plate the former having a diameter smaller than the internal diameter of the impacter chamber. This apparatus comprises means for ensuring the downward vertical circulation of the air and means, identical in each stage, for rotating each perforated plate relative to the corresponding collection disk. The invention is characterized in that the axis of each collection disk is offset with respect to the axis of the perforated corresponding plate.

Various embodiments are envisaged for bringing about this offsetting. The offsetting is such that the deposits of particles collected on the collection disks cover wide annular surfaces, with adjacent annular surfaces being juxtaposed such that the deposited particles are homogenously spread over virtually the entire surface area of the disk.

The main advantages of the invention are that the deposit collected on the collection disk and coming from all the holes located on the same circumference, the circumferences being coaxial to the axis of the perforated plate, uniformly covers a larger annular surface than the deposition surfaces of the prior art. Provided that two adjacent circles constituted by identically calibrated holes are sufficiently close to one another, the annular deposition surfaces of each are juxtaposed. Thus, there is a uniform deposition of the particles over the entire collection disk.

Modifications to the impaction characteristics of a given stage are no longer necessary. Thus, as a result of the substantially constant deposit thickness, the distance between the opening and the collection point is not subject to variation. The reentrainment of the aerosol from one stage to the next is consequently reduced. Moreover, the phenomenon of the auto-absorption of particles (particularly α-particles in the case of α-radioactivity counting) is greatly reduced as a result of the fact that relatively fewer particles are superimposed.

According to a first embodiment of the present invention, the offset collection disk is fixed to a toothed circular plate having a diameter larger than the diameter of the collection disk, with discharge of the aerosol occurring through holes made in that part of the plate not covered by the collection disk. This toothed plate, mounted in a circular groove formed in the cylindrical body of each stage, engages two pinions, the first of which is integral with the lower end of a rod rotated by a motor. The first pinion transmits the rotary movement to the second pinion by means of two lugs mounted on its outer face which fit into two openings machined on the outer face of the second pinion. The second pinion is itself integral with the upper end of a coaxial rod which is identical to the rod of the preceding stage.

According to a second embodiment of the invention, each collection disk corresponding to a given stage pivots about its axis on a thrust ball bearing, which bearing is mobile within a cup concentric to the cylindrical chamber of the impacter and to the perforated plate, this cup being supported by a brace having several arms, the ends of which are fitted into the cylindrical body of the impacter.

In this embodiment, each collection disk, weighted by a counterweight fixed to the periphery of its lower face, is offset by sloping the impacter in such a way that the disk always has its counterweight at the lowest point.

The rotation of the impacter body by means of a motor brings about rotation of the perforated plate in each stage relative to the offset, stationary collection disk.

According to a third embodiment, each collection disk is mounted on a thrust ball bearing, which is offset with respect to the impacter body. The bearing pivots on a flat support secured by a brace having several branches, the ends of which are fitted into the cylindrical body of the impacter.

In this embodiment, each collection disk is provided with magnetic counterweights fixed at two diametrically opposite peripheral positions or in the vicinity of the periphery at two diametrally opposite positions. Each disk is rotated under the action of an external rotary magnetic field, for example, produced by a magnetic coil located outside the cylindrical chamber of the impacter.

BRIEF DESCRIPTION OF THE DRAWINGS

The invention is described in greater detail hereinafter relative to non-limitative embodiments and the attached drawings, wherein.

DETAILED DESCRIPTION OF THE PREFERRED EMBODIMENTS

Figure 1A:
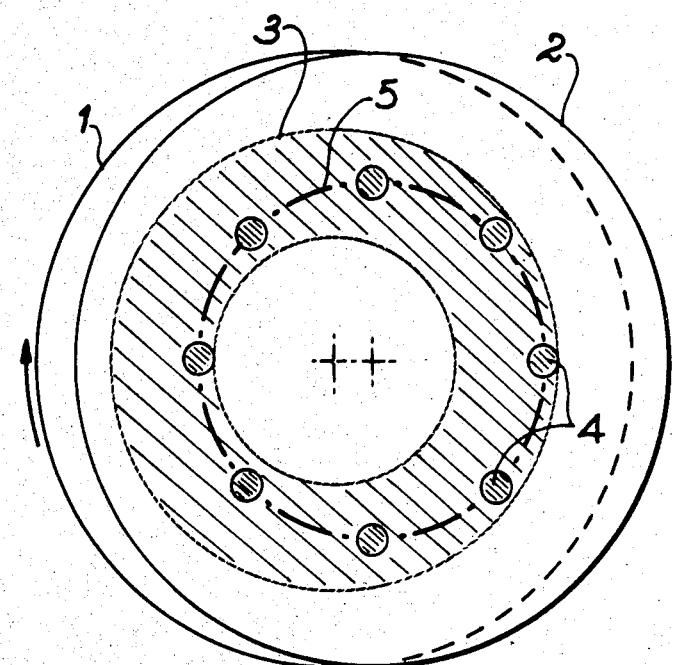
FIG. 1a is a plan view of the offset of the collection disk relative to the perforated plate, with the hatched area indicating the annular area of deposition.
Figure 1B:
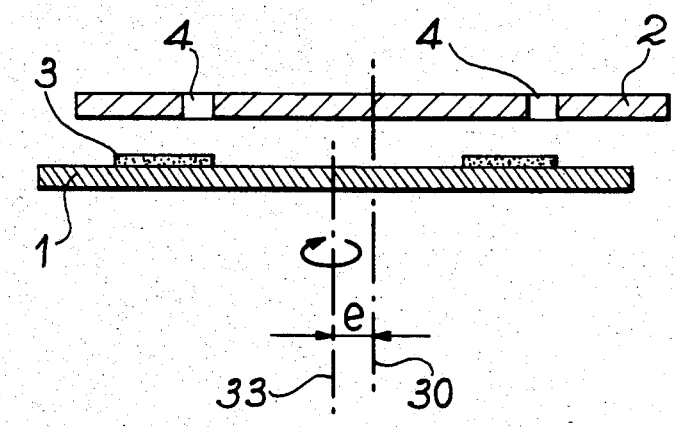
FIG. 1b is a sectional view of the disk and plate as well as the distribution of the deposit on the collection disk.

As stated hereinbefore, the first embodiment of the present invention makes use of the rotation of the collection disk 1, which is offset with respect to the perforated circular plate 2, illustrated in FIGS. 1a and 1b. The hatched area 3 represents the area of deposition of the particles impacted on collection disk 1, which rotates about axis 33 in accordance with FIG. 1b, following passage of the particles through identically calibrated openings 4 arranged along one of the circumferences 5 coaxial to axis 30 of perforated plate 2. Area 3 covers an annular surface having a width substantially equal to twice the offset e plus the diameter of opening 4. By correctly fixing the distance between successive circumferences 5, the juxtaposition of each annular surface 3 deposited from each of the holes or openings 4 arranged along the same circumference 5 leads to the homogenization of the deposit over the entire surface of disk 1.

Figure 2:
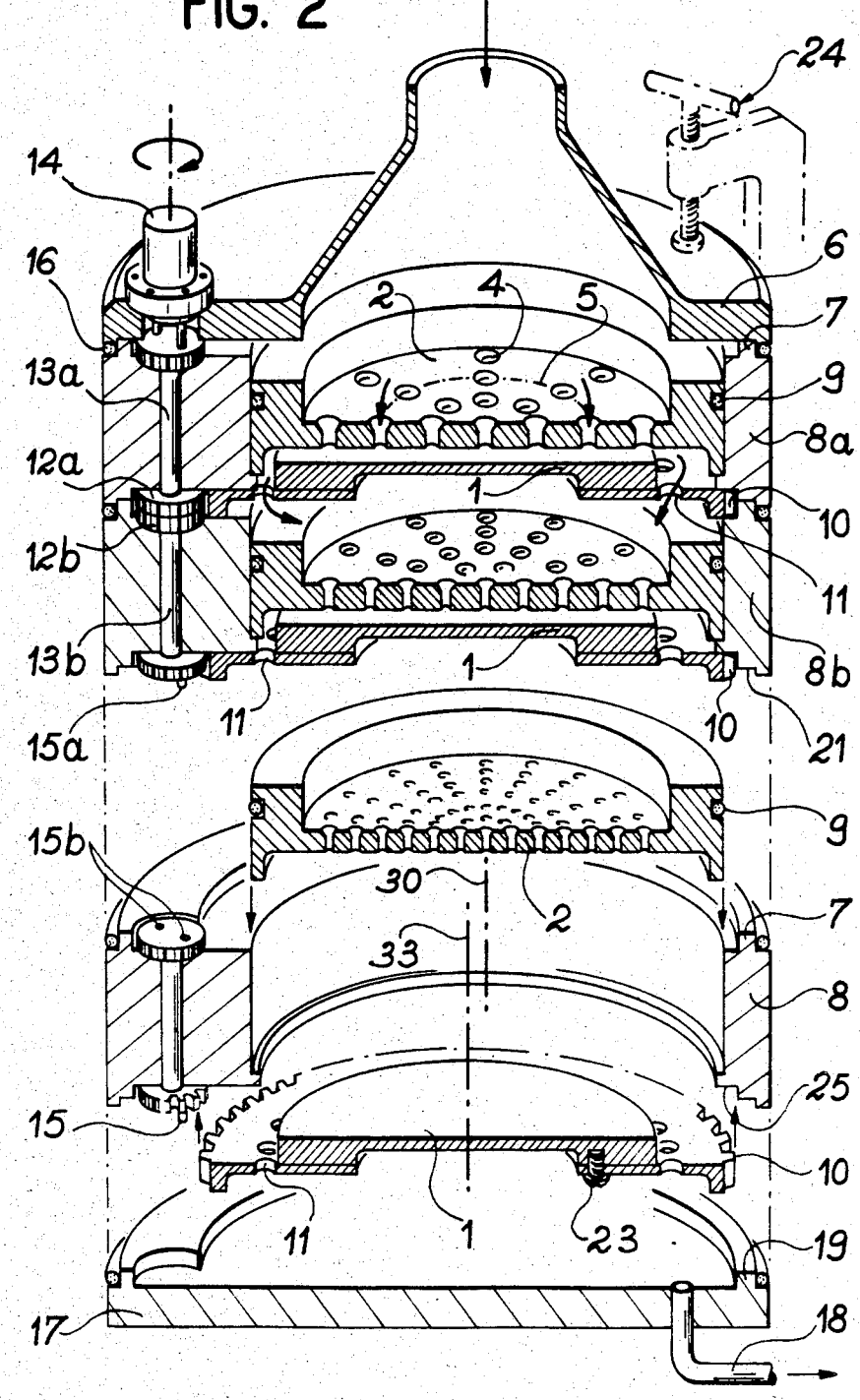
FIG. 2 is a sectional perspective view of the first embodiment showing a gear system for rotating the collection disks.

FIG. 2 shows a cascade impacter having an aerosol admission cone and a cylindrical base 6, which is keyed onto a circular joggle 7, located in the upper part of a tight, hollow, cylindrical chamber of revolution constituted by the superimposing of several stages in the form of hollow cylinders of revolution 8. All of the stages are traversed by the aerosol flow from the admission cone 6. Each hollow cylinder, i.e. stage, 8 has a circular plate 2, perforated by holes 4 located on concentric circles 5 coaxial to the circular plate and having an identical diameter, which hole diameter decreases progressively for successive stages. Each plate 2 is tightly fitted by means of an O-ring 9 into the cylindrical body of stage 8. Each stage 8 also has a collection disk 1 located downstream of the perforated plate 2, having a diameter smaller than the internal diameter of the cylindrical body of stage 8, on which the particles are deposited by impaction.

As a result of their inertia, the heavier particles impact on the first collection disk 1, the other particles overflowing the periphery of the rotating disk and thus reaching the following stage 8 by way of holes 11. According to the prior art, the dimensional category of the particles collected in each stage depended on the velocity of the jet through the openings of the stage in question, on the distance between the collection disk 1 and the openings 4, and finally on the collection characteristics of the preceding stage. Moreover, maintaining a constant flow rate in the impacter through openings having a continuously decreasing diameter increases the speed of the air as it flows downward through the impacter, which leads to the progressive impaction of ever finer particles towards the lower stages. The final stage forms a highly efficient filter, which collects all the ultrafine particles not trapped in the preceding stages.

The purified air is discharged by way of a pipe 18 formed in the flat-bottomed base cylinder 17. The upper part of cylinder 17 has a circular joggle 19, onto which is tightly fitted the lower portion of the last stage. Pipe 18 carries a pump (not shown) which ensures the flow of air through the apparatus. In the lower part of each stage, there is a circular notch 21, in which is fitted the circular joggle 7 machined on the upper part of the following stage. A screw clamp-type system 24 is used for assembling the stages. Sealing between the stages is ensured by O-rings 16.

In a first embodiment of the invention, the offset rotation of collection disk 1 with respect to the axis of perforated plate 2 is brought about by using a set of gears. Each collection disk 1 is fixed by means of screws 23 to a circular toothed plate 10 of larger diameter which has on those portions of its upstream face not covered by the disk, openings 11 for discharging the particles from one stage towards the lower stage.

Each toothed plate 10 is installed in a circular groove 25 made in the interior of the cylindrical body of the sampler. It engages two pinions 12a, 12b imparting thereto its offset rotary movement with respect to the axis of perforated plate 2. Pinion 12a, which is fixed to the lower end of a rod 13a rotated by a motor 14, transmits its rotary movement to pinion 12b by means of two lugs 15a mounted on its lower face and fitted into two openings 15b formed on the upper face of pinion 12b, which is in turn joined to the upper end of a rod 13b belonging to the following stage 8b. Rod 13b is coaxial and identical to rod 13a of the preceding stage 8a. Thus, all the collection disks 1 rotate at the same speed about the same axis 33, which is offset compared with axis 30 of perforated plates 2.

This embodiment has the advantage of having stages which are easily disassembled due to the fact that they are independent of one another. The number of stages can vary according to the invention. Moreover, an apparatus of this type could also have been considered for rotating the perforated plates, the collecting plates remaining fixed.

Figure 3:
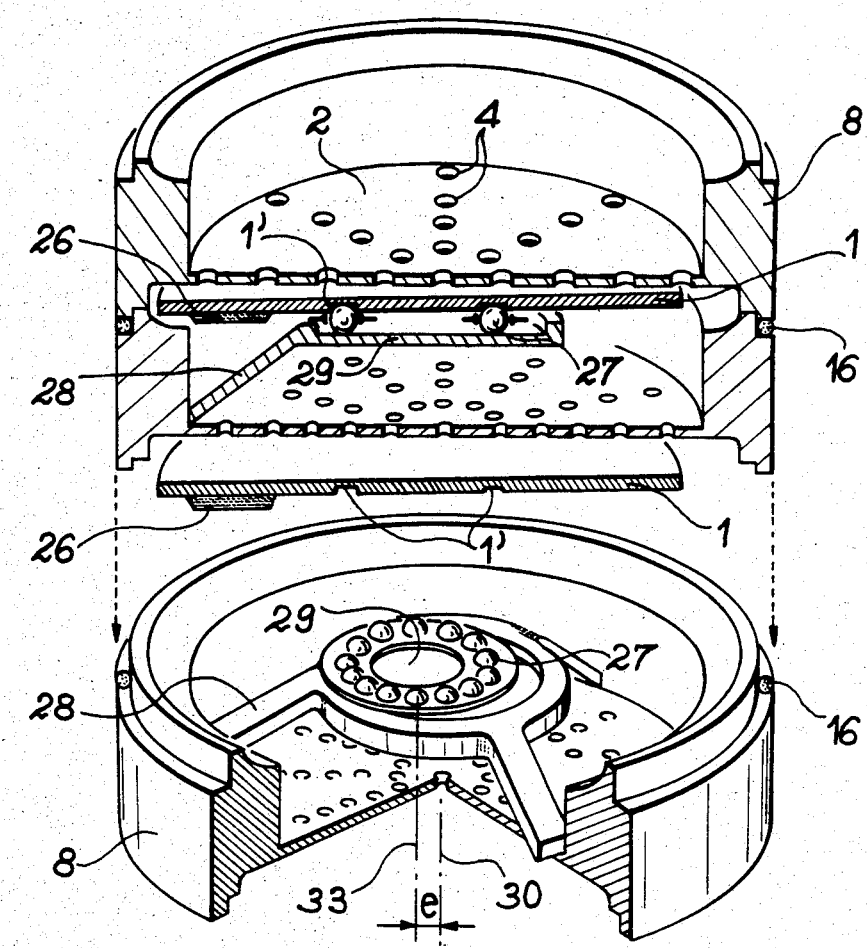
FIG. 3 is a sectional perspective view of the second embodiment with a thrust ball bearing on which is mounted the collection disk, the disk being weighted by a counterweight fixed to the periphery of its downstream face.

FIG. 3 shows a second embodiment for the rotation of the collection plates. It consists of using a thrust ball bearing 27 to which is fitted the collection disk 1, positioned by means of a groove 1', in such a way that disk 1 and thrust ball bearing 27 are concentric. Thrust ball bearing 27 can move laterally within a flat-bottomed cup 29. The internal diameter of the cup is equal to the external diameter of the thrust ball bearing, plus twice the desired offset. The cup 29 is supported by a brace having three branches 28, whose ends bear on the circular plate perforated by holes 2 and against the wall of the hollow cylindrical chamber 8 of the lower stage. Cup 29, perforated plate 2 and chamber 8 are concentric.

Each collection disk 1 is weighted by a counterweight 26 fixed to the periphery of its lower face. By slightly inclining the body of the corresponding chamber 8, each collection disk 1 is positioned in such a way that counterweight 26 remains at the lowest point, which brings about the desired offset of collection disk 1 relative to perforated plate 2. The impacter body is then rotated by any known means, e.g. a motor. This second embodiment has a simpler construction, but assumes the rotation of the entire impacter body, the axis of revolution of which will be inclined relative to the vertical axis.

Figure 4:
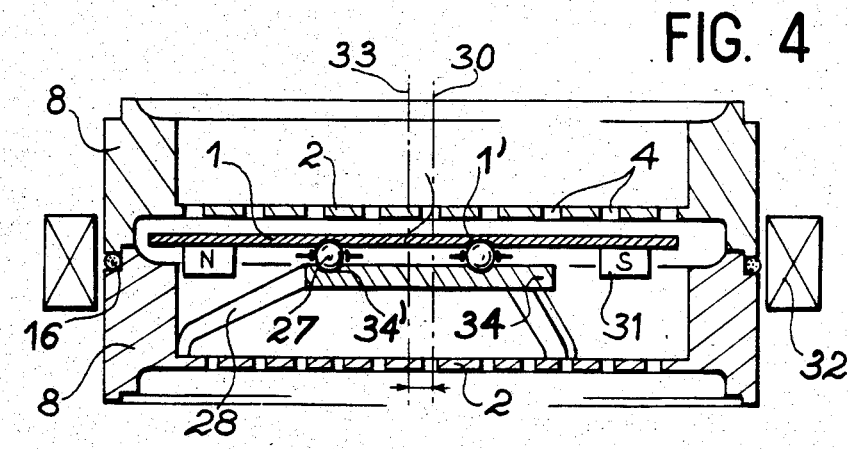
FIG. 4 is a sectional view of the third embodiment, characterized by the fitting of the magnetic counterweights in the vicinity of two diametrically opposite peripheral positions on the collection disk and a magnetic coil arranged outside the impacter.

FIG. 4 shows a third embodiment, which is a variant of the preceding embodiment. The thrust ball bearing 27 pivots in a groove 34' cut on a flat cylindrical support 34 supported by a brace with three branches 28, as shown hereinbefore. Groove 34' is cut in such a way that the rotation axis 33 of the thrust ball bearing 27, and consequently of collection plate 1, is offset relative to the axis of symmetry 30 of the whole impacter. The collection disk 1, which has been previously magnetized by magnetic counterweights 31 fixed to two diametrically opposite ends, is rotated under the action of a rotary external magnetic field, e.g. produced by a magnetic coil 32 positioned outside cylindrical chamber 8.

The third embodiment also has a simpler construction than the first embodiment, however, it is not suitable for collecting magnetic aerosols. It also assumes that the other components of the impacter are non-magnetic, as is the case with the aluminum alloy Andersen compacter.

The second and third embodiments are preferred in comparison with the first, because they can be realized on any cascade-type impaction apparatus of the type used without any modification other than the addition of the aforementioned elements. Thus, the impacter can be reused in its original version for purposes not requiring a uniform deposition, as permitted by the present invention.

A final embodiment (not depicted) consists of using the flow of air in the impacter for rotating offset disks peripherally provided with blades.

The use of these different embodiments permitting the obtaining of a homogeneous deposit of particles on collection disks and the maximum utilization of said disks can be extended to known applications of the cascade impacter, namely the granulometric separation of radioactive aerosols with a view to analysis by $\alpha$-counting or $\alpha$-spectrometry ($PuO_2$ or dust), very high concentration combustion aerosols and aerosols with a view to analysis by gravimetry, microscopy, X-fluorescence and chemical analysis.

What is claimed is:

1. An apparatus of the aerosol sampler type with cascade impaction and uniform deposition comprising a conical air inlet fixed to a tight, hollow, cylindrical chamber of revolution constituted by the superimposing of several stages in the form of hollow cylinders of revolution traversed by the air flow from the conical inlet and each having a circular plate perforated with holes located on concentric circles coaxial to said plate and having an identical diameter progressively decreasing in each stage, as well as a collection disk located downstream of the perforated plate and whose diameter is smaller than the internal diameter of the impacter chamber, incorporating means for ensuring the vertical downward circulation of the air and means for the relative rotation of each perforated plate with respect to the corresponding collection disk, wherein in each stage, the axis of rotation of the disk passes through the disk and is offset relative to the axis of the circular perforated plate.

2. An apparatus according to claim 1, wherein the offset collection disk is fixed to a circular toothed plate having a diameter larger than the diameter of the collection disk, the aerosol being discharged by holes made in that part of the plate not covered by the collection disk and mounted in a circular groove made within the cylindrical body of the impacter stage engaging on two pinions, whereof the first, which is integral with the lower end of a rod rotated by a motor, transmits the rotary movement to the second by means of two lugs, which are mounted on its outer face and which fit into two openings made on the outer face of the second pinion, which is fixed to the upper end of a rod, forming a component of the following stage, which is coaxial and identical to the rod of the preceding stage.

3. An apparatus according to claim 1, wherein each collection disk is mounted on a thrust ball bearing, movable within a cap supported by a brace having a plurality of branches, whereof the ends are fitted into the cylindrical body of the impacter.

4. An apparatus according to claim 3, wherein each collection disk is weighted by a counterweight fixed to the periphery of its lower face.

5. A process for realising the apparatus according to claim 4, wherein each collection disk is offset by inclining and rotating the impacter.

6. An apparatus according to claim 1, wherein each collection disk is mounted on an offset thrust ball bearing pivoting on a support held by a brace having several branches, whereof the ends are fitted into the cylindrical body of the impacter.

7. An apparatus according to claim 6, wherein each collection disk provided with magnetic counterweights fixed to two diametrically opposite ends of the disk or in the vicinity thereof is rotated about its axis under the action of a rotary external magnetic field produced by a magnetic coil positioned outside the cylindrical chamber of the impacter.

8. An apparatus of the aerosol sampler type utilizing cascade impaction and uniform deposition, comprising a plurality of stages connected in a cascade arrangement, each of said stages including:
 (a) a casing with a substantially cylindrical bore of predetermined diameter, said bores communicating in series;
 (b) a perforated plate fixedly mounted in said casing bore and having a plurality of holes of equal diameter, said holes being arranged along a plurality of concentric circles coaxial with an axis of symmetry of said perforated plate;
 (c) a collection means rotatably mounted in said casing bore and having a collection disk, and coupling means for producing rotation of said collection disk, said collection disk having a diameter smaller than said predetermined diameter of said casing bore, and
 (d) a drive means coupled to said coupling means for rotating said collection disk;

wherein the holes of a perforated plate in any one of said stages have a diameter which is less than the diameter of the holes of a perforated plate in the previous stage of said cascade arrangement,
said apparatus further comprising a conical air inlet means attached to a first stage in said plurality of stages and communicating with the casing bore thereof, and a base plate attached to a last stage in said plurality of stages and having an air outlet means formed therein;
the improvement wherein the axis of rotation of the collection disk in each of said stages passes through said collection disk and is offset relative to the axis of symmetry of the perforated plate in the same stage.

9. The apparatus of claim 8, wherein said coupling means comprises a toothed plate on which said corresponding collection disk is mounted, said toothed plate having a plurality of holes formed therein, said holes being arranged on the periphery of said collection disk.

* * * * *